(12) United States Patent
Majima et al.

(10) Patent No.: US 8,674,073 B2
(45) Date of Patent: Mar. 18, 2014

(54) IMMUNOGLOBULIN AFFINITY LIGAND

(75) Inventors: Eiji Majima, Tokushima (JP); Atsushi Shima, Tokushima (JP); Yuko Hara, Tokushima (JP)

(73) Assignee: Protenova Co., Ltd., Naruto-shi (JP)

( * ) Notice: Subject to any disclaimer, the term of this patent is extended or adjusted under 35 U.S.C. 154(b) by 922 days.

(21) Appl. No.: 12/280,221

(22) PCT Filed: Feb. 21, 2007

(86) PCT No.: PCT/JP2007/053189
§ 371 (c)(1),
(2), (4) Date: Aug. 21, 2008

(87) PCT Pub. No.: WO2007/097361
PCT Pub. Date: Aug. 30, 2007

(65) Prior Publication Data
US 2010/0286373 A1 Nov. 11, 2010

(30) Foreign Application Priority Data

Feb. 21, 2006 (JP) .................................. 2006-043358

(51) Int. Cl.
*C07K 1/00* (2006.01)
*A23J 1/00* (2006.01)

(52) U.S. Cl.
USPC ............................. 530/350; 530/412; 530/413

(58) Field of Classification Search
None
See application file for complete search history.

(56) References Cited

U.S. PATENT DOCUMENTS 6,740,734 B1 * 5/2004 Nilsson et al. ................. 530/350
2005/0143566 A1 * 6/2005 Hober .......................... 530/388.4

FOREIGN PATENT DOCUMENTS

JP 2006-304633 A 11/2006

OTHER PUBLICATIONS

Machine Translation of JP 2006-304633 A.*

International Search Report of PCT/JP2007/053189, date of mailing May 15, 2007.
Ladaviere, Catherine et al.; "Covalent Immobilization of Proteins onto (Maleic Anhydride-alt-methyl Vinyl Ether) Copolymers: Enhanced Immobilization of Recombinant Proteins"; Bioconjugate Chemistry, 1998, vol. 9, No. 6, pp. 655-661.
Allard Laure et al.; "Mechanisms Leading to an Oriented Immobilization of Recombinant Proteins Derived from the P24 Capsid of HIV-1 onto Copolymers"; Bioconjugate Chemistry, 2001, vol. 12, No. 6, pp. 972-979.
Allard Laure et al.; "Versatile Method for Production and Controlled Polymer-Immobilization of Biologically Active Recombinant Proteins"; Biotechnology and Bioengineering, 202, vol. 80, No. 3, pp. 341-348.
Tashiro, Mitsuru et al.; "High-resolution Solution NMR Structure of the Z Domain of *Staphylococcal* Protein A"; Journal of Molecular Biology, 1997, vol. 272, No. 4, pp. 573-590.
Jendeberg L. et al.; "Kinetic Analysis of the Interaction Between Protein A Domain Variants and Human Fc Using Plasmon Resonance Detection"; Journal of Molecular Recognition, 1995, vol. 8, No. 4, pp. 270-278.
Scaramozzino F. et al.; "Improvement of Catalytic Properties of *Escherichia coli* Penicillin G Acylase Immobilized on Glyoxyl Agarose by Addition of a Six-Amino-Acid Tag"; Applied and Environmental Microbiology, 2005, vol. 71, No. 12, pp. 8937-8940.

* cited by examiner

*Primary Examiner* — Daniel E Kolker
*Assistant Examiner* — James Rogers
(74) *Attorney, Agent, or Firm* — Westerman, Hattori, Daniels & Adrian, LLP

(57) ABSTRACT

Provided is affinity chromatography carrier for an immunoglobulin that simultaneously has high immunoglobulin-binding capability and chemical stability and that can be produced at low cost. An immunoglobulin-binding protein in which an amino acid substitution for not only maximizing the number of lysine residues on the protein surface of helix 3 and its periphery but also minimizing the number of lysine residues present on the protein surfaces of helix 1 and helix 2 as immunoglobulin-binding regions and/or an amino acid substitution for eliminating an aspartic acid-proline sequence have (has) been carried out, or a multimer thereof, is used as an affinity ligand for an affinity chromatography carrier.

12 Claims, 6 Drawing Sheets

Fig. 1

AATTCTAGACTAGTTGCATCTTAAGTGTAGCTAGCCATCACCATCACCACCATTAATAATAAGCTTGGATCC
    GATCTGATCAACGTAGAATTCACATCGATCGGTAGTGGTAGTGGTGGTAATTATTATTCGAACCTAGGTCGA
    /       /         /         /                                /        /
EcoRI    SpeI      AflII      NheI                           HindIII    BamHI

Fig. 2

M  A  Q  H  D  E  A  S  A  D  N  K  F  N  K  E  Q  Q  N  A  F  Y  E  I  L  H
aattctcatATGGCACAGCACGACGAAGCTAGTGCGGATAACAAATTTAACAAAGAACAGCAGAATGCGTTTTATGAGATTCTGCAT
    gagtaTACCGTGTCGTGCTGCTTCGATCACGCCTATTGTTTAAATTGTTTCTTGTCGTCTTACGCAAAATACTCTAAGACGTA
   /     /
EcoRI   NdeI L  P  N  L  T  E  E  Q  R  N  A  F  I  Q  S  L  K  D  D  P  S  V  S  K  E  I  L  A  E
CTGCCGAACCTGACCGAAGAACAGCGCAATGCATTTATCCAGAGCCTTAAGGACGATCCCAGCGTGAGCAAAGAGATCTTAGCGGAA
GACGGCTTGGACTGGCTTCTTGTCGCGTTACGTAAATAGGTCTCGGAATTCCTGCTAGGGTCGCACTCGTTTCTCTAGAATCGCCTT
                                           /                              /
                                         AflII                           BglII A  K  K  L  N  D  A  Q  A  P  K  A  S  H  H  H  H  H  H  *  *  *
GCGAAAAAGCTGAACGACGCCCAGGCCCCGAAAGCTAGCCATCACCATCACCACCATTAATAATAAgcttg
CGCTTTTTCGACTTGCTGCGGGTCCGGGGCTTTCGATCGGTAGTGGTAGTGGTGGTAATTATTATTcgaacctag
                              /                            /      /
                             NheI                        HindIII  BamHI

SEQUENCE LISTING

```
<160> NUMBER OF SEQ ID NOS: 39

<210> SEQ ID NO 1
<211> LENGTH: 58
<212> TYPE: PRT
<213> ORGANISM: Staphylococcus aureus
<220> FEATURE:
<223> OTHER INFORMATION: Protein A mutated immunoglobulin-binding
      domain(C-domain + G29A)

<400> SEQUENCE: 1

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
```

```
                    35                  40                  45

Lys Lys Leu Asn Asp Ala Gln Ala Pro Lys
        50                  55

<210> SEQ ID NO 2
<211> LENGTH: 58
<212> TYPE: PRT
<213> ORGANISM: Staphylococcus aureus
<220> FEATURE:
<223> OTHER INFORMATION: Protein A mutated immunoglobulin-binding
      domain(Z-domain + V1A)

<400> SEQUENCE: 2

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
        50                  55

<210> SEQ ID NO 3
<211> LENGTH: 61
<212> TYPE: PRT
<213> ORGANISM: Artificial Sequence
<220> FEATURE:
<223> OTHER INFORMATION: modified immunoglobulin-binding protein
<220> FEATURE:
<221> NAME/KEY: MUTAGEN
<222> LOCATION: (37)..(37)
<223> OTHER INFORMATION: Glu or Ala or Ile or Leu or Ser or Thr

<400> SEQUENCE: 3

Ala Asp Asn Ala Phe Asn Thr Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Xaa Pro Ser Lys Ser Lys Ile Leu Lys Glu Ala
        35                  40                  45

Lys Lys Leu Asn Lys Ala Gln Ala Pro Lys Lys Lys Lys
        50                  55                  60

<210> SEQ ID NO 4
<211> LENGTH: 72
<212> TYPE: DNA
<213> ORGANISM: Artificial Sequence
<220> FEATURE:
<223> OTHER INFORMATION: Designed oligonucleotide shown in Figure 1

<400> SEQUENCE: 4
aattctagac tagttgcatc ttaagtgtag ctagccatca ccatcaccac cattaataat     60
aagcttggat cc                                                         72

<210> SEQ ID NO 5
<211> LENGTH: 245
<212> TYPE: DNA
<213> ORGANISM: Artificial Sequence
<220> FEATURE:
<223> OTHER INFORMATION: DNA sequence of modified immunoglobulin-binding
      protein shown in Figure 2
<220> FEATURE:
<221> NAME/KEY: CDS
<222> LOCATION: (10)..(231)
<223> OTHER INFORMATION: MAQHDEASADNKFNKEQQNAFYEILHLPNLTEEERNAFIQSLKDDPS
```

VSKEILAEAKKLNDAQAPKASHHHHHH

<400> SEQUENCE: 5

```
aattctcat atg gca cag cac gac gaa gct agt gcg gat aac aaa ttt aac        51
          Met Ala Gln His Asp Glu Ala Ser Ala Asp Asn Lys Phe Asn
           1               5                  10 aaa gaa cag cag aat gcg ttt tat gag att ctg cat ctg ccg aac ctg          99
Lys Glu Gln Gln Asn Ala Phe Tyr Glu Ile Leu His Leu Pro Asn Leu
 15              20                  25                  30 acc gaa gaa cag cgc aat gca ttt atc cag agc ctt aag gac gat ccg         147
Thr Glu Glu Gln Arg Asn Ala Phe Ile Gln Ser Leu Lys Asp Asp Pro
                 35                  40                  45 agc gtg agc aaa gag atc tta gcg gaa gcg aaa aag ctg aac gac gcc         195
Ser Val Ser Lys Glu Ile Leu Ala Glu Ala Lys Lys Leu Asn Asp Ala
                     50                  55                  60 cag gcc ccg aaa gct agc cat cac cat cac cac cat taataataagcttg          245
Gln Ala Pro Lys Ala Ser His His His His His His
             65                  70
```

<210> SEQ ID NO 6
<211> LENGTH: 74
<212> TYPE: PRT
<213> ORGANISM: Artificial Sequence
<220> FEATURE:
<223> OTHER INFORMATION: Amino acid sequence of modified immunoglobulin-
      binding protein shown in Figure 2

<400> SEQUENCE: 6

```
Met Ala Gln His Asp Glu Ala Ser Ala Asp Asn Lys Phe Asn Lys Glu
 1               5                  10                  15

Gln Gln Asn Ala Phe Tyr Glu Ile Leu His Leu Pro Asn Leu Thr Glu
             20                  25                  30

Glu Gln Arg Asn Ala Phe Ile Gln Ser Leu Lys Asp Asp Pro Ser Val
         35                  40                  45

Ser Lys Glu Ile Leu Ala Glu Ala Lys Lys Leu Asn Asp Ala Gln Ala
     50                  55                  60

Pro Lys Ala Ser His His His His His His
 65                  70
```

<210> SEQ ID NO 7
<211> LENGTH: 27
<212> TYPE: DNA
<213> ORGANISM: Artificial Sequence
<220> FEATURE:
<223> OTHER INFORMATION: Designed U primer listed in Table 1

<400> SEQUENCE: 7
ccgaattctc atatggcaca gcacgac        27

<210> SEQ ID NO 8
<211> LENGTH: 28
<212> TYPE: DNA
<213> ORGANISM: Artificial Sequence
<220> FEATURE:
<223> OTHER INFORMATION: Designed R primer listed in Table 1

<400> SEQUENCE: 8
ctggatccaa gcttattatt aatggtgg        28

<210> SEQ ID NO 9
<211> LENGTH: 21
<212> TYPE: DNA
<213> ORGANISM: Artificial Sequence
<220> FEATURE:

-continued

```
<223> OTHER INFORMATION: Designed U primer listed in Table 1

<400> SEQUENCE: 9
agccttaagg acgaacccag c                                              21

<210> SEQ ID NO 10
<211> LENGTH: 21
<212> TYPE: DNA
<213> ORGANISM: Artificial Sequence
<220> FEATURE:
<223> OTHER INFORMATION: Designed U primer listed in Table 1

<400> SEQUENCE: 10
agccttaagg acgctcccag c                                              21

<210> SEQ ID NO 11
<211> LENGTH: 21
<212> TYPE: DNA
<213> ORGANISM: Artificial Sequence
<220> FEATURE:
<223> OTHER INFORMATION: Designed U primer listed in Table 1

<400> SEQUENCE: 11
agccttaagg acattcccag c                                              21

<210> SEQ ID NO 12
<211> LENGTH: 21
<212> TYPE: DNA
<213> ORGANISM: Artificial Sequence
<220> FEATURE:
<223> OTHER INFORMATION: Designed U primer listed in Table 1

<400> SEQUENCE: 12
agccttaagg accttcccag c                                              21

<210> SEQ ID NO 13
<211> LENGTH: 21
<212> TYPE: DNA
<213> ORGANISM: Artificial Sequence
<220> FEATURE:
<223> OTHER INFORMATION: Designed U primer listed in Table 1

<400> SEQUENCE: 13
agccttaagg acaccccag c                                               21

<210> SEQ ID NO 14
<211> LENGTH: 26
<212> TYPE: DNA
<213> ORGANISM: Artificial Sequence
<220> FEATURE:
<223> OTHER INFORMATION: Designed R primer listed in Table 1

<400> SEQUENCE: 14
gctaagatct ctttgctctt gctggg                                         26

<210> SEQ ID NO 15
<211> LENGTH: 21
<212> TYPE: DNA
<213> ORGANISM: Artificial Sequence
<220> FEATURE:
<223> OTHER INFORMATION: Designed R primer listed in Table 1

<400> SEQUENCE: 15
tccgctaaga tcttttttgct c                                             21

<210> SEQ ID NO 16
```

```
<211> LENGTH: 27
<212> TYPE: DNA
<213> ORGANISM: Artificial Sequence
<220> FEATURE:
<223> OTHER INFORMATION: Designed U primer listed in Table 1

<400> SEQUENCE: 16
aaagagatct taaaggaagc gaaaaag                                         27

<210> SEQ ID NO 17
<211> LENGTH: 33
<212> TYPE: DNA
<213> ORGANISM: Artificial Sequence
<220> FEATURE:
<223> OTHER INFORMATION: Designed R primer listed in Table 1

<400> SEQUENCE: 17
gatggctagc tttcggggcc tgtttgtcgt tca                                  33

<210> SEQ ID NO 18
<211> LENGTH: 36
<212> TYPE: DNA
<213> ORGANISM: Artificial Sequence
<220> FEATURE:
<223> OTHER INFORMATION: Designed R primer listed in Table 1

<400> SEQUENCE: 18
gatggctagc tttcggggcc tgggctttgt tcagct                               36

<210> SEQ ID NO 19
<211> LENGTH: 30
<212> TYPE: DNA
<213> ORGANISM: Artificial Sequence
<220> FEATURE:
<223> OTHER INFORMATION: Designed R primer listed in Table 1

<400> SEQUENCE: 19
gatggctagc tttcggtttc tgggcgtcgt                                      30

<210> SEQ ID NO 20
<211> LENGTH: 31
<212> TYPE: DNA
<213> ORGANISM: Artificial Sequence
<220> FEATURE:
<223> OTHER INFORMATION: Designed R primer listed in Table 1

<400> SEQUENCE: 20
gatggctagc cttttctttt ttcggggcct g                                    31

<210> SEQ ID NO 21
<211> LENGTH: 34
<212> TYPE: DNA
<213> ORGANISM: Artificial Sequence
<220> FEATURE:
<223> OTHER INFORMATION: Designed R primer listed in Table 1

<400> SEQUENCE: 21
gatggctagc tttcggtttc tgggctttgt tcag                                 34

<210> SEQ ID NO 22
<211> LENGTH: 21
<212> TYPE: DNA
<213> ORGANISM: Artificial Sequence
<220> FEATURE:
<223> OTHER INFORMATION: Designed U primer listed in Table 2

<400> SEQUENCE: 22
```
gcggataacg catttaacaa a                                          21

<210> SEQ ID NO 23
<211> LENGTH: 21
<212> TYPE: DNA
<213> ORGANISM: Artificial Sequence
<220> FEATURE:
<223> OTHER INFORMATION: Designed R primer listed in Table 2

<400> SEQUENCE: 23
tttgttaaat gcgttatccg c                                          21

<210> SEQ ID NO 24
<211> LENGTH: 21
<212> TYPE: DNA
<213> ORGANISM: Artificial Sequence
<220> FEATURE:
<223> OTHER INFORMATION: Designed U primer listed in Table 2

<400> SEQUENCE: 24
tttaacaccg aacagcagaa t                                          21

<210> SEQ ID NO 25
<211> LENGTH: 21
<212> TYPE: DNA
<213> ORGANISM: Artificial Sequence
<220> FEATURE:
<223> OTHER INFORMATION: Designed R primer listed in Table 2

<400> SEQUENCE: 25
ctgctgttcg gtgttaaatt t                                          21

<210> SEQ ID NO 26
<211> LENGTH: 21
<212> TYPE: DNA
<213> ORGANISM: Artificial Sequence
<220> FEATURE:
<223> OTHER INFORMATION: Designed U primer listed in Table 2

<400> SEQUENCE: 26
tttaaccgcg aacagcagaa t                                          21

<210> SEQ ID NO 27
<211> LENGTH: 21
<212> TYPE: DNA
<213> ORGANISM: Artificial Sequence
<220> FEATURE:
<223> OTHER INFORMATION: Designed R primer listed in Table 2

<400> SEQUENCE: 27
ctgctgttcg cggttaaatt t                                          21

<210> SEQ ID NO 28
<211> LENGTH: 21
<212> TYPE: DNA
<213> ORGANISM: Artificial Sequence
<220> FEATURE:
<223> OTHER INFORMATION: Designed U primer listed in Table 2

<400> SEQUENCE: 28
cagagccttg cggacgatcc c                                          21

<210> SEQ ID NO 29
<211> LENGTH: 21
<212> TYPE: DNA
<213> ORGANISM: Artificial Sequence
<220> FEATURE:

<223> OTHER INFORMATION: Designed R primer listed in Table 2

<400> SEQUENCE: 29
gggatcgtcc gcaaggctct g                                    21

<210> SEQ ID NO 30
<211> LENGTH: 21
<212> TYPE: DNA
<213> ORGANISM: Artificial Sequence
<220> FEATURE:
<223> OTHER INFORMATION: Designed U primer listed in Table 2

<400> SEQUENCE: 30
cagagccttc atgacgatcc c                                    21

<210> SEQ ID NO 31
<211> LENGTH: 21
<212> TYPE: DNA
<213> ORGANISM: Artificial Sequence
<220> FEATURE:
<223> OTHER INFORMATION: Designed R primer listed in Table 2

<400> SEQUENCE: 31
gggatcgtca tgaaggctct g                                    21

<210> SEQ ID NO 32
<211> LENGTH: 21
<212> TYPE: DNA
<213> ORGANISM: Artificial Sequence
<220> FEATURE:
<223> OTHER INFORMATION: Designed U primer listed in Table 2

<400> SEQUENCE: 32
cagagcctta atgacgatcc c                                    21

<210> SEQ ID NO 33
<211> LENGTH: 21
<212> TYPE: DNA
<213> ORGANISM: Artificial Sequence
<220> FEATURE:
<223> OTHER INFORMATION: Designed R primer listed in Table 2

<400> SEQUENCE: 33
gggatcgtca ttaaggctct g                                    21

<210> SEQ ID NO 34
<211> LENGTH: 21
<212> TYPE: DNA
<213> ORGANISM: Artificial Sequence
<220> FEATURE:
<223> OTHER INFORMATION: Designed U primer listed in Table 2

<400> SEQUENCE: 34
cagagccttc aggacgatcc c                                    21

<210> SEQ ID NO 35
<211> LENGTH: 21
<212> TYPE: DNA
<213> ORGANISM: Artificial Sequence
<220> FEATURE:
<223> OTHER INFORMATION: Designed R primer listed in Table 2

<400> SEQUENCE: 35
cagagccttc aggacgatcc c                                    21

<210> SEQ ID NO 36

```
<211> LENGTH: 21
<212> TYPE: DNA
<213> ORGANISM: Artificial Sequence
<220> FEATURE:
<223> OTHER INFORMATION: Designed U primer listed in Table 2

<400> SEQUENCE: 36
cagagccttc gtgacgatcc c                                                   21

<210> SEQ ID NO 37
<211> LENGTH: 21
<212> TYPE: DNA
<213> ORGANISM: Artificial Sequence
<220> FEATURE:
<223> OTHER INFORMATION: Designed R primer listed in Table 2

<400> SEQUENCE: 37
gggatcgtca cgaaggctct g                                                   21

<210> SEQ ID NO 38
<211> LENGTH: 21
<212> TYPE: DNA
<213> ORGANISM: Artificial Sequence
<220> FEATURE:
<223> OTHER INFORMATION: Designed U primer listed in Table 2

<400> SEQUENCE: 38
cagagccttt atgacgatcc c                                                   21

<210> SEQ ID NO 39
<211> LENGTH: 21
<212> TYPE: DNA
<213> ORGANISM: Artificial Sequence
<220> FEATURE:
<223> OTHER INFORMATION: Designed R primer listed in Table 2

<400> SEQUENCE: 39
gggatcgtca taaaggctct g                                                   21
```

IMMUNOGLOBULIN AFFINITY LIGAND

TECHNICAL FIELD

The present invention relates to a protein having affinity for an immunoglobulin, and more specifically, to a modified protein obtained by modifying an immunoglobulin-binding protein so as to have improved properties as an affinity ligand for affinity chromatography. The present invention also relates to a use of the modified protein as an immunoglobulin affinity ligand and a use of the modified protein for an affinity separation matrix.

DEFINITION

In the present invention, the term "protein" refers to any molecule having a peptide structure and includes a variant obtained by artificially modifying a partial fragment of a natural protein or a sequence of the natural protein. The term "immunoglobulin-binding domain" refers to a functional unit of a polypeptide having immunoglobulin-binding activity on its own, and the term "immunoglobulin-binding protein" refers to a protein having specific affinity for an immunoglobulin and including an "immunoglobulin-binding domain" that binds noncovalently to an immunoglobulin.

The term "functional variant" of an immunoglobulin-binding protein refers to an immunoglobulin-binding protein that is obtained by modification such as addition, deletion, or substitution of partial amino acid or chemical modification of amino acid residues, and has at least 80%, preferably at least 90% homology with an unmodified amino acid sequence, and it is evaluated as equivalent to an unmodified protein in terms of functional properties including immunoglobulin-binding activity.

The term "affinity ligand" refers to a molecule having an ability to bind to a specific molecule by specific affinity, and in the present invention, the term refers to an immunoglobulin-binding protein capable of selectively binding to an immunoglobulin. Note that the affinity ligand may be simply referred to as "ligand". The term "affinity chromatography carrier" refers to a carrier obtained by immobilizing an affinity ligand on an insoluble carrier. The immobilization is achieved by binding an affinity ligand covalently to an insoluble carrier, and the insoluble carrier can be used as an adsorbent having affinity for a target molecule (immunoglobulin).

The phrase "improved orientation for maintaining affinity for an immunoglobulin" in immobilization of a ligand on an insoluble carrier refers to an increased ratio of ligand molecules that are immobilized in a direction that allows the molecule to bind to an immunoglobulin, resulting in an increased number of immunoglobulin molecules capable of binding to a unit number of ligand molecules immobilized.

BACKGROUND ART

In recent years, highly pure protein reagents or protein drugs are highly demanded for researches in the biotechnology-related field or in the pharmaceutical industry. In a method of producing a highly pure protein, purification processes based on various principles such as hydrophobic chromatography, gel filtration chromatography, and ion exchange chromatography may be employed. Affinity chromatography is a particularly excellent method because of being capable of separating a target protein from foreign substances and of concentrating the protein at remarkably high efficiency. In the affinity chromatography, the target protein is separated from foreign substances by adsorbing the protein on an insoluble carrier including, as a ligand, a molecule having specific affinity for the protein, and the protein is used as the ligand molecule in some cases.

Protein A is a protein derived from Staphylococcus aureus and has a repeated structure including five immunoglobulin-binding domains having homology to each other, called E-domain, D-domain, A-domain, B-domain, and C-domain. An immunoglobulin-binding domain is known to bind singly to an immunoglobulin (Non-Patent Document 1), and a recombinant protein including only immunoglobulin-binding domains having a partially-modified amino acid sequence is widely used as the affinity ligand for the affinity chromatography, along with a natural protein A. The Staphylococcus is known to express a protein capable of binding to an immunoglobulin other than the protein A (Patent Document 1), and a partial structure of the protein other than the protein A includes a region in an amino acid sequence having about 45% homology to an immunoglobulin-binding domain of the protein A. However, the availability of this immunoglobulin-binding domain as the affinity ligand, such as chemical stability under acidic and alkaline pH conditions, is unknown.

As for the protein A, in order to provide an adsorptive medium having chemical stability, which is at least equal to or higher than that of another adsorbent based on bonding specificity to IgG, a bonding amount, and the natural protein A, there has been suggested a technique for using, as the ligand, the protein A (rProtein A cys) where one cysteine residue has been introduced and immobilizing the protein A via a thioester bond on an affinity carrier at one point. Moreover, in order to solve problems of the chemical stability on an immobilization site, which is an issue of an affinity carrier for antibody purification such as affinity chromatography carrier where the Protein A cys has been immobilized and problems of sterilization/washing steps due to the chemical stability, and in order to adsorb antibody molecules in larger amounts, there has been suggested a technique for immobilizing the molecules in a C-terminal carboxyl group selective manner via an amide bond on a carrier where a polymer compound having a primary amino group has been introduced (Patent Document 3).

Patent Document 4 further suggests: an immunoglobulin-binding protein that can, for example, be derived from a protein capable of binding to other regions of the immunoglobulin molecule other than the complementary determining regions (CDR), such as B-domain of Staphylococcal protein A, in which at least one asparagine residue has been mutated to an amino acid other than a glutamine or aspartic acid, which mutation confers an increased chemical stability at pH-values of up to about 13 to 14 compared to the parental molecule; and a matrix for affinity separation, which includes the protein as a ligand coupled to a solid carrier. The best embodiment for imparting alkali resistance shown in this document is a combination of substitution of a threonine for the aspartic acid at position 23 and substitution of a glutamic acid for the asparagine at position 43.

Patent Document 1: U.S. Pat. No. 6,548,639 B1
Patent Document 2: U.S. Pat. No. 6,399,750 B1 (JP 2000-500649 A)
Patent Document 3: JP 2005-112827 A
Patent Document 4: WO 03/080655 (JP 2005-538693 A)
Non Patent Document 1: Nilsson B et al., Protein engineering, 1987, vol. 1(2), 107-113

DISCLOSURE OF THE INVENTION

Problems to be Solved by the Invention

An affinity chromatography carrier to be used in a production process of an immunoglobulin serving as a material of an antibody drug has properties required for general chromatography carriers, such as hardness enough to bear high flow rate or weight of the gel, and desirably has the following properties: (a) it can bind to an immunoglobulin in a larger amount per unit weight or unit volume of the carrier; (b) it releases only a small amount of a ligand in a process for eluting an immunoglobulin under acidic pH conditions; (c) reduction of immunoglobulin-binding activity in a process for washing a line under alkaline pH conditions is low; and (d) it can be produced at low cost. In particular, the property (a) is important for reducing a cost of immunoglobulin purification. In order to solve the problems, it is obviously important to select an appropriate material of an insoluble carrier or a method of producing a ligand protein, and it is extremely important to improve an immunoglobulin-binding protein to be used as a ligand.

Although various studies for improving the properties (a) to (d) have been made, examples of improvement achieved by modifying a ligand protein itself include (a) and (c). The similarity between techniques (Patent Documents 2 and 3) developed for producing a carrier that is excellent in the property (a) is immobilization of a ligand protein on a carrier at one point in the C-terminal or its periphery, and the techniques have problems in that the carrier easily releases a ligand protein cleaved in a process for eluting an immunoglobulin under acidic pH conditions or a fragment thereof. In order to produce a carrier excellent in the property (b), it is known that a method of immobilizing a ligand protein on a carrier at many points, as opposed to (a), is effective, and the protein is generally immobilized on a carrier via a plurality of primary amino groups present in a protein A molecule. However, when a ligand protein is immobilized by the method, orientation of the protein cannot be controlled, and immobilized ligand proteins include molecules that cannot bind to an immunoglobulin, resulting in a decreased binding amount of an immunoglobulin per unit weight or unit volume of the carrier. That is, in existing techniques, the properties (a) and (b) are opposite factors, and a novel technique for achieving both properties has been required. In a disclosed technique (Patent Document 4) for producing a carrier excellent in the property (c), chemical stability thereof is not yet enough. Meanwhile, a typical commercially available affinity chromatography carrier for an immunoglobulin includes a protein A-protein mainly produced by genetic engineering technique, and the production method is required to be improved.

An object of the present invention is to provide a modified protein, in which the property as an affinity ligand for affinity chromatography is modified in an immunoglobulin-binding protein, that is, being excellent in both the opposite properties (a) and (b) and in the property (c). A further object of the present invention is to provide a use of the modified protein as an immunoglobulin affinity ligand and to provide a use of the protein in an affinity separation matrix, that is, to provide an affinity chromatography carrier that has high immunoglobulin-binding ability and chemical stability and can be produced at low cost.

Means for Solving the Problems

In the case where a ligand protein is immobilized on an affinity chromatography carrier by crosslinking the protein at one point so that orientation is easily controlled, the ligand protein or a peptide fragment is easily released due to cleavage of the crosslinking site or peptide chain. On the other hand, in the case where an immunoglobulin-binding domain protein of protein A, which is generally used, is immobilized as a ligand on a carrier at many points, the carrier is hard to release the ligand protein. However, orientation of the ligand cannot be controlled, and the binding amount of the immunoglobulin per volume of the carrier is small. The inventors of the present invention achieved the above-described opposite factors by modifying a ligand protein so that orientation can be controlled in crosslinking even if the protein is immobilized on a carrier at many points.

As described above, one molecule of a protein A-protein derived from *Staphylococcus* includes five immunoglobulin-binding domains, and each of the immunoglobulin-binding domains is composed of three a-helix structures and two loop structures obtained by ligating the three a-helix structures to each other. All of ten amino acids that are considered to be directly involved in a bond with Fc region of an immunoglobulin are present in a helix located on the first position from the N-terminal (helix 1) and a helix located on the second position from the N-terminal (helix 2) (Tashiro M. et al., 1997, High-resolution solution NMR structure of the Z domain of staphyrococcal protein A, Journal of Molecular Biology vol. 272 (4), p. 573-590). Moreover, the immunoglobulin-binding domains can bind to an immunoglobulin even if helix 3 is deleted (Melissa A. et al., 1997, Structural mimicry of a native protein by a minimized binding domain. Proceeding Natural Academy of Sciences USA, vol. 94, p. 10,080-10,085).

In a general reaction for immobilizing a protein on an affinity chromatography carrier, main active groups in the protein to be used in a reaction for binding the protein to the carrier include thiol groups of cysteine, amino groups of an N-terminal amino acid and lysine, carboxyl groups of a C-terminal amino acid, glutamic acid, and aspartic acid, and the like. The inventors of the present invention focused attention on a lysine residue as an amino acid residue suitable for control of orientation and binding to a carrier at many points, and the inventors designed arrangement of lysine in the molecule of protein A based on data of the three-dimensional structure of an immunoglobulin-binding domain of protein A. Specifically, the inventors studied amino acid substitution for not only maximizing the number of lysine residues on the protein surfaces of helix 3 and its periphery but also minimizing the number of lysine residues present on the protein surfaces of helix 1 and helix 2 as immunoglobulin-binding regions. In addition, the inventors of the present invention studied substitution for eliminating an aspartic acid-proline sequence, which was considered to be easily cleaved under acidic pH conditions, to prevent release of a ligand protein in a process for eluting an immunoglobulin under acidic pH conditions.

The inventors of the present invention have searched on a ligand protein excellent in many aspects by evaluating prepared modified proteins in terms of behaviors in cation exchange chromatography, sensitivity to cleavage under acidic pH conditions, immunoglobulin-binding activities when the protein is immobilized on a chromatography carrier, and stability under alkaline pH conditions. As a result, the inventors have succeeded in producing a modified immunoglobulin-binding protein that can be purified easily as a ligand protein itself, has a high immunoglobulin-binding activity even when immobilized on a carrier at many points, and is very stable under acidic pH and alkaline pH conditions, thus completing the present invention.

That is, the scope of the present invention includes a modified protein in a functional variant of an immunoglobulin-binding protein according to any of the following items (1) to (9).

(1) A modified protein or a functional variant thereof, which is an immunoglobulin-binding protein capable of binding to a region other than a complementary determining region (CDR) of an immunoglobulin molecule, in which a modified protein of a C-domain of *Staphylococcus* protein A specified by SEQ ID NO: 1 or a Z-domain specified by SEQ ID NO: 2 has (A) improved orientation for maintaining affinity for an immunoglobulin in immobilization of the protein on an insoluble carrier via an amino group of the protein as compared to an unmodified molecule because a ratio of the number of lysine at positions 39 onwards to the number of lysine at positions 1 to 38 is increased as compared to a ratio in the unmodified molecule and/or (B) improved chemical stability under acidic pH conditions as compared to the chemical stability of the unmodified molecule because an aspartic acid-proline sequence is eliminated.

The item (1) includes: an aspect of a modified protein characterized in that an immunoglobulin-binding protein represented by SEQ ID NO: 1 or 2 or a functional variant thereof has (A) improved orientation for maintaining affinity for an immunoglobulin in immobilization of the protein on an insoluble carrier via an amino group of the protein as compared to an unmodified molecule because a ratio of the number of lysine at positions 39 onwards to the number of lysine at positions 1 to 38 is increased as compared to a ratio in the unmodified molecule; an aspect of a modified protein characterized in that an immunoglobulin-binding protein represented by SEQ ID NO: 1 or 2 or a functional variant thereof has (B) improved chemical stability under acidic pH conditions as compared to that of the unmodified molecule because an aspartic acid-proline sequence is eliminated; and an aspect of a modified protein characterized in that an immunoglobulin-binding protein represented by SEQ ID NO: 1 or 2 or a functional variant thereof has (A) improved orientation for maintaining affinity for an immunoglobulin in immobilization of the protein on an insoluble carrier via an amino group of the protein as compared to an unmodified molecule because a ratio of the number of lysine at positions 39 onwards to the number of lysine at positions 1 to 38 is increased as compared to a ratio in the unmodified molecule and (B) improved chemical stability under acidic pH conditions as compared to a ratio of the unmodified molecule because an aspartic acid-proline sequence is eliminated.

(2) The (A) is a modified protein or a functional variant thereof according to the item (1), in which the (A) is achieved by substitution of lysine at positions 39 onwards, and/or modification for addition of a lysine, and/or modification for substitution of other amino acid for lysine originally present at positions 4, 7, and 35.

The item (2) is an aspect including (A) in the item (1), which includes: an aspect of substitution of lysine at positions 39 onwards; an aspect of addition of a lysine; an aspect of substitution of other amino acid for lysine originally present at positions 4, 7, and 35; an aspect of substitution of lysine for amino acid at positions 39 onwards and addition of a lysine; an aspect of substitution of lysine for amino acid at positions 39 onwards and substitution of other amino acid for lysine originally present at positions 4, 7, and 35; an aspect of substitution of lysine for amino acid at positions 39 onwards, addition of a lysine, and substitution of other amino acid for lysine originally present at positions 4, 7, and 35; and an aspect of addition of a lysine and substitution of other amino acid for lysine originally present at positions 4, 7, and 35.

(3) A modified protein or a functional variant thereof according to the item (2), in which the substitution of lysine for amino acid at positions 39 onwards is substitution of a lysine for 1 to 6 of amino acid at positions 40, 43, 46, 53, 54, and 56.

(4) A modified protein or a functional variant thereof according to the item (2), in which the modification for substitution of other amino acid for lysine originally present at positions 4, 7, and 35 is substitution of an alanine, glutamine, asparagine, valine, serine, threonine, histidine, tyrosine, or arginine for amino acid at positions 4, 7, and 35.

(5) A modified protein or a functional variant thereof according to the item (2), in which the modification for addition of a lysine residue is modification for addition of 1 to 5 lysine residues to the C-terminal.

(6) A modified protein or a functional variant thereof according to the item (1), in which the (B) is achieved by modification for substitution of an amino acid other than an aspartic acid for the aspartic acid at position 37 or modification for substitution of an amino acid other than a proline for the proline residue at position 38.

The item (6) is an aspect including (B) in the item (1), which includes: an aspect of modification for substitution of an amino acid other than an aspartic acid for the aspartic acid at position 37; an aspect of modification for substitution of an amino acid other than a proline for the proline at position 38; and an aspect of modification for substitution of an amino acid other than an aspartic acid for the aspartic acid at position 37 and modification for substitution of an amino acid other than a proline for the proline at position 38.

(7) A modified protein or a functional variant thereof according to the item (6), in which the modification for substitution of an amino acid other than an aspartic acid residue for the aspartic acid at position 37 is substitution of an alanine, glutamic acid, serine, threonine, leucine, or isoleucine for the amino acid at position 37.

(8) A modified protein or a functional variant thereof according to the item (6), in which the modification for substitution of an amino acid other than a proline for the proline at position 38 is substitution of an alanine, serine, or threonine for the amino acid at position 38.

(9) A modified protein or a functional variant thereof characterized by including an amino acid sequence specified by SEQ ID NO: 3.

Besides, the scope of the present invention includes a multimer in the item (10) below.

(10) A multimer characterized by including ligation of 2 to 5 immunoglobulin-binding protein units, which include the modified protein or a functional variant thereof according to any one of the item (1) to (9).

Besides, the scope of the present invention includes a nucleic acid in the item (11) below.

(11) A nucleic acid encoding the modified protein, the functional variant thereof, or the multimer including it according to any one of items (1) to (10).

Note that the term "multimer including it" refers to "multimer including a modified protein or a functional variant thereof".

Besides, the scope of the present invention includes a gene expression system in the item (12) below.

(12) A gene expression system including the nucleic acid according to the item (11).

Besides, the scope of the present invention includes an affinity chromatography carrier in the item (13) below.

(13) An affinity chromatography carrier including, as an affinity ligand, the modified protein, the functional variant thereof, or the multimer including it according to any one of the items (1) to (10).

Besides, the scope of the present invention includes an affinity column in the item (14) below.

(14) An affinity column including the affinity chromatography carrier according to the item (13).

Besides, the scope of the present invention includes an affinity separation method in the item (15) below.

(15) An affinity separation method for IgG, IgA, and/or IgM characterized by using the affinity column according to the item (14).

Besides, the scope of the present invention includes a protein chip in the item (16) below.

A protein chip including the modified protein, the functional variant thereof, or the multimer including it according to any one of the items (1) to (10).

Effect of the Invention

According to the present invention, it is possible to provide an affinity chromatography carrier, which has high immunoglobulin-binding capability and chemical stability and a little leakage of a ligand protein. More specifically, the present invention provides (a) an affinity carrier capable of binding to a larger amount of an immunoglobulin per unit weight or unit volume of the carrier by modifying a modified protein of C-domain of protein A or Z domain specified by SEQ ID NO: 2 so that a ratio of the number of lysine at positions 39 onwards to the number of lysine at positions 1 to 38 is increased as compared to that of an unmodified molecule, whereby the protein can be immobilized on an insoluble carrier selectively via amino groups at positions 39 onwards, resulting in improved orientation as an immunoglobulin affinity ligand as compared to the unmodified molecule (described in Example 7). Moreover, such modification enables immobilization of the protein on an insoluble carrier via a plurality of amino groups and elimination of an aspartic acid-proline sequence, so that the present invention can provide an affinity carrier having both (b) chemical stability under acidic pH conditions (described in Example 3) and (c) chemical stability under alkaline pH conditions (described in Example 8). Further, the modification of the present invention facilitates purification of the protein by cation exchange chromatography because of increased positive charge on the protein surface, so that the present invention can provide (d) a ligand protein that can be produced at low cost (described in Example 2).

In addition, a use of the modified protein as an immunoglobulin affinity ligand enables affinity purification of an immunoglobulin that has high immunoglobulin-binding capability and chemical stability and is inexpensive, so that the present invention can provide a product containing an immunoglobulin at low cost.

BRIEF DESCRIPTION OF THE DRAWINGS

FIG. 1 A drawing showing the nucleotide sequence of a synthetic oligonucleotide used in construction of the plasmid pUCASR1.

FIG. 2 A drawing showing the nucleotide sequence encoding an immunoglobulin-binding protein constructed in the plasmid pUC/SPAC' and the amino acid sequence thereof.

BEST MODE FOR CARRYING OUT THE INVENTION

Figure 3:
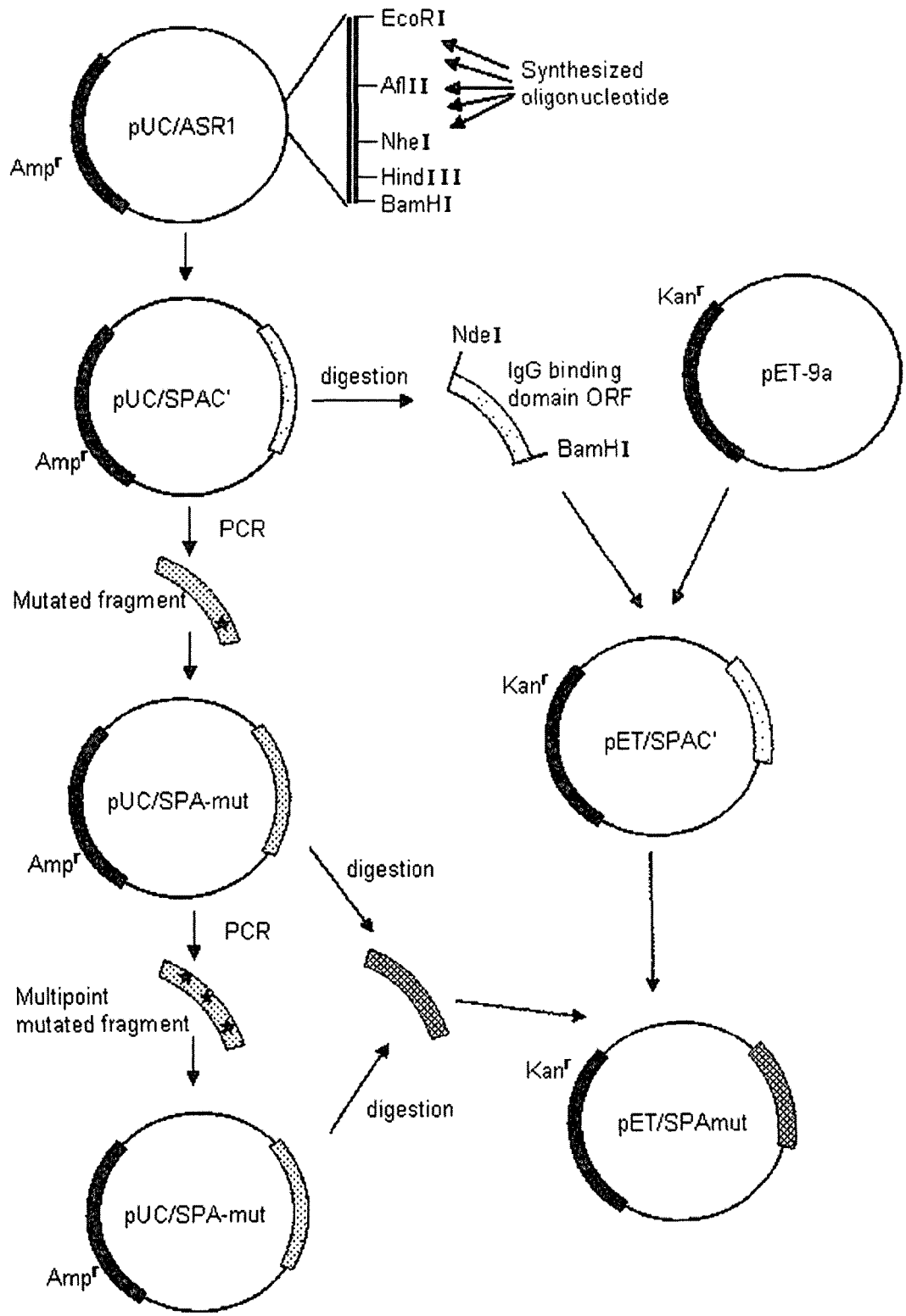
FIG. 3 A drawing showing procedures of construction of a plasmid expressing an immunoglobulin-binding protein.

Examples of a standard technique for producing an immunoglobulin-binding protein of the present invention include known genetic engineering techniques described in, for example, Current Protocols In Molecular Biology by Frederick M. Ausbel et al. and the like. That is, the protein can be obtained from cultured cells in a large amount at a low cost by transforming a host such as *Escherichia coli* with an expression vector including a nucleotide sequence encoding a target modified protein and culturing the cells in an appropriate liquid medium. Specifically, one immunoglobulin-binding domain of protein A is a small protein including about 60 amino acids. Therefore, a DNA encoding a target amino acid sequence is divided into synthetic oligonucleotides including several tens of bases, and the oligonucleotides are synthesized and ligated with a DNA ligase by a ligation reaction, followed by insertion into a plasmid vector, to thereby prepare a target expression vector. In this procedure, in order to express the protein in *Escherichia coli* efficiently, a person skilled in the art usually employs a nucleotide sequence including an optimum codon of *Escherichia coli*. The amino acid sequence of an unmodified immunoglobulin-binding domain may be an amino acid sequence of any of all domains of protein A. However, among five domains, a C-domain including many lysine residues at positions 39 onwards is preferably used, and the sequence of C-domain (shown in SEQ ID NO: 1 in Sequence Listing) subjected to substitution of an alanine for the glycine at position 29 (see Non-patent Document 1), which is known to improve chemical stability, is most preferably used, though a sequence of a Z-domain that has been actually used as an affinity ligand for an immunoglobulin in a high degree may be used. A DNA sequence mutation for achieving the target amino acid substitution can be easily introduced into an intended site by an overlap extension method using an unmodified clone DNA as a template and using, as primers, synthetic oligo-DNAs including mismatched base pairs in a polymerase chain reaction, a cassette mutation method, or the like.

Besides, in the case of using an immunoglobulin-binding protein derived from protein A as an affinity chromatography ligand for an immunoglobulin, a multimer protein obtained by ligating two or more, desirably about four immunoglobulin-binding domains has been conventionally produced and used. Also in the case of an immunoglobulin-binding protein obtained in the present invention, a multimer protein obtained by ligating two or more, desirably about four immunoglobulin-binding domains is preferably produced and used. A cDNA encoding such a multimer protein can be easily prepared by ligating the intended number of cDNAs each encoding one immunoglobulin-binding domain in series. A multimer protein obtained by ligating two or more of immunoglobulin-binding domain units can be easily produced by using such a cDNA inserted into an appropriate expression plasmid.

The expression vector to be inserted with a nucleotide sequence encoding the modified protein of the present invention may be any vector capable of replicating itself in a host cell, such as a plasmid, phage, or virus. Examples of a commercially available expression vector include pQE vector (QIAGEN GmbH), pDR540 and pRIT2T (GE Healthcare Bio-Sciences KK), and pET vector (Merck Ltd.). The expression vector is preferably used in appropriate combination with a host cell. For example, in the case of using *Escherichia coli* as a host cell, a combination of the pET vector and an *Escherichia coli* strain BL21 (DE3) or a combination of the pDR540 vector and an *Escherichia coli* strain JM109 is preferable.

A modified protein of the present invention can be collected in a soluble fraction by collecting cultured cells by centrifugation or the like and breaking the cells by a treatment of sonication, French press, or the like. Purification of the modified protein can be performed by using known separation/purification techniques in appropriate combination. Specifically, the techniques include: separation techniques such as salting-out, dialysis, and ultrafiltration; and purification methods such as hydrophobic chromatography, gel filtration chromatography, ion exchange chromatography, affinity chromatography, and reverse-phase chromatography. The modified protein of the present invention is obtained by modification for decreasing negative charge and increasing positive charge on its surface and has a characteristic of the isoelectric point higher than that of each of many contaminating proteins derived from a cell of a host such as *Escherichia coli*. Therefore, in a purification process, ion exchange chromatography is particularly desirably employed.

Examples of an insoluble carrier for binding to the modified protein of the present invention as an immunoglobulin affinity ligand include: natural polymer materials such as chitosan and dextran; and synthetic polymers such as vinyl polymer, highly crosslinked agarose, and polyimide. In another embodiment, the carrier may be an inorganic carrier such as silica. In general, a ligand protein is immobilized on a carrier with: a coupling agent such as cyanogen bromide, epichlorohydrin, N-hydroxysuccinimide, tosyl/tresyl chloride, carbodiimide, glutaraldehyde, or hydrazine; a carboxyl- or thiol-activated carrier; or the like. Such coupling reactions are well known in the technical field and described in various documents (for example, Jansson, J. C. and Ryden, L., "Protein purification", 2nd edition, p. 375-442, ISBN 0-471-18626-0). A ligand protein of the present invention is characterized in that the protein binds to a carrier via a plurality of amino groups arranged so that orientation of the ligand can be spatially controlled. The protein can be immobilized on a carrier having an active group capable of forming a covalent bond by a reaction with an amino group of the protein, such as a tresyl, epoxy, carboxyl, or formyl group. Examples of a commercially-available carrier include TOYOPEARL AF-tresyl-650, TOYOPEARL AF-epoxy-650, TOYOPEARL AF-carboxy-650, TOYOPEARL AF-formyl-650 (TOSOH CORPORATION), NHS-activated Sepharose, cyanogen bromide-activated Sepharose, and epoxy-activated Sepharose (GE Healthcare Bio-Sciences KK).

The affinity carrier of the present invention prepared as above can be used for affinity chromatography in a process for isolating and purifying an immunoglobulin such as IgA, IgG, or IgM after the carrier is filled in an appropriate column.

In another embodiment, an immunoglobulin-binding protein of the present invention can be used for binding to immunoglobulin after the protein is immobilized on a base such as capillary, tip, or filter. In this procedure, the reaction for immobilizing the protein on a base is desirably a reaction with an active group capable of forming a covalent bond by a reaction with an amino group of the protein in the same way as the case of immobilization on an affinity chromatography carrier.

Hereinafter, the present invention will be described specifically by way of examples, but the present invention is not limited thereto.

First, the inventors of the present invention evaluated ease of purification processes from behaviors of modified proteins expressed as proteins with His-tag in cation exchange chromatography and evaluated stability of purified modified proteins under acidic pH conditions. Next, the inventors prepared and purified modified proteins added with no His-tag and immobilized the proteins on a chromatography carrier to create affinity chromatography gels, and evaluated immunoglobulin-binding activities and stability under alkaline conditions of the gels.

EXAMPLE 1

[Construction of Plasmid for Expressing Immunoglobulin-Binding Protein with His-Tag]

First, two pairs of double-stranded DNA fragments obtained from four synthetic oligonucleotides were ligated, and a DNA fragment having the sequence shown in FIG. 1 (SEQ ID NO: 4 in Sequence Listing) was cloned in the plasmid pUC19 (NIPPON GENE CO., LTD.) with EcoRI and HindIII, to thereby prepare pUC/ASR1.

Next, three pairs of double-stranded DNA fragments obtained from six synthetic oligonucleotides were ligated to the site between EcoRI-AflII restriction enzyme cleavage sites in the plasmid, and two pairs of double-stranded DNA fragments obtained from four synthetic oligonucleotides were ligated to the site between AflII-NheI restriction enzyme cleavage sites, followed by cloning, to thereby prepare pUC/SPAC', a plasmid including DNA sequences (SEQ ID NOS: 5 and 6) of an immunoglobulin-binding protein shown in FIG. 2 (a protein with substitution of an alanine for the glycine at position 29 in C-domain (corresponding to SEQ ID NO: 1 in Sequence Listing; hereinafter, referred to as SPAC')).

Thereafter, the plasmid was cleaved with NdeI and BamHI to create a cDNA fragment encoding a protein, and the fragment was incorporated into a plasmid pET-9a (Merck Ltd.), to thereby prepare a plasmid for expressing SPAC', pET/SPAC' (FIG. 3).

Subsequently, in order to construct a plasmid encoding a variant with substitution in one amino acid, PCR was performed using a pair of synthetic oligonucleotides shown in Table 1 as primers and using the plasmid pUC/SPAC' as a template, to thereby prepare cDNA fragments each including a target mutation. The enzyme and apparatus used in PCR were PrimeSTAR HS DNA polymerase (TAKARA BIO INC.) and PCR Thermal Cycler SP (TAKARA BIO INC.), respectively.

Then, the fragments were incorporated into the plasmid pUC/SPAC' with the restriction enzymes each shown in Table 1, to thereby prepare variant plasmids of V40K, E43K, A46K, D53K, A54K, A56K, and 59-61K where three lysine were inserted into the C-terminal.

PCR was performed using the thus-prepared plasmid encoding a variant with substitution in one amino acid as a template to prepare cDNA fragments of a variant including amino acid substitutions on a plurality of sites, and the fragments were incorporated with the restriction enzymes each shown in Table 1 into a plasmid having a mutation on another site, to thereby construct a plasmid with substitution in two or more amino acid.

Table 1 shows combinations of PCR primers used for construction of plasmids encoding variants with amino acid substitution, plasmids used as templates and subcloning vectors, and restriction enzymes used in incorporation of DNA fragments. Sequence numbers of the primers each represent the numbers in Sequence Listing.

The nucleotide sequences of the sites encoding recombinant proteins in the expression plasmids were determined using CEQ 8000 DNA sequencer (Beckman Coulter, Inc.).

TABLE 1

| Variant with His-tag | Sequence number of U-primer | Sequence number of R-primer | Template cDNA | Subcloning plasmid | Restriction enzyme |
|---|---|---|---|---|---|
| D37E | 9 | 8 | pUC/SPAC' | pUC/SPAC' | AflII, BamHI |
| D37A | 10 | 8 | pUC/SPAC' | pUC/SPAC' | AflII, BamHI |
| D37I | 11 | 8 | pUC/SPAC' | pUC/SPAC' | AflII, BamHI |
| D37L | 12 | 8 | pUC/SPAC' | pUC/SPAC' | AflII, BamHI |
| D37T | 13 | 8 | pUC/SPAC' | pUC/SPAC' | AflII, BamHI |
| V40K | 7 | 14 | pUC/SPAC' | pUC/SPAC' | EcoRI, BglII |
| E43K | 7 | 15 | pUC/SPAC' | pUC/SPAC' | EcoRI, BglII |
| A46K | 16 | 8 | pUC/SPAC' | pUC/SPAC' | BglII, HindIII |
| A54K | 7 | 17 | pUC/SPAC' | pUC/ASR1 | EcoRI, NheI |
| D53K | 7 | 18 | pUC/SPAC' | pUC/ASR1 | EcoRI, NheI |
| A56K | 7 | 19 | pUC/SPAC' | pUC/ASR1 | EcoRI, NheI |
| 59-61K | 7 | 20 | pUC/SPAC' | pUC/ASR1 | EcoRI, NheI |
| A46K, A54K | 7 | 17 | pUC/A46K | pUC/ASR1 | EcoRI, NheI |
| V40K, E43K, A46K | 7 | 15 | pUC/V40K | pUC/A46K | EcoRI, BglII |
| E43K, A46K, A54K | 7 | 15 | pUC/SPAC' | pUC/A46K, A54K | EcoRI, BglII |
| V40K, E43K, A46K, D53K | 7 | 18 | pUC/V40K, E43K, A46K | pUC/ASR1 | EcoRI, NheI |
| V40K, E43K, A46K, D53K, A56K | 7 | 21 | pUC/V40K, E43K, A46K | pUC/ASR1 | EcoRI, NheI |

EXAMPLE 2

[Study on Expression of Immunoglobulin-Binding Protein with His-Tag and Purification Process]

BL21 (DE3) competent cells (Merck Ltd.) were transformed with the respective expression plasmids constructed above, to thereby prepare bacterial strains each capable of expressing modified proteins.

Each of the *Escherichia coli* strains was inoculated in a 2× TY medium containing 25 mg/L kanamycin and cultured at 37° C. for 16 hours to express a target protein, and centrifugation was performed to collect *Escherichia coli* cells.

Thereafter, the collected *Escherichia coil* cells were suspended in 50 mM MES buffer (pH 6.0), and sonication was performed to break the *Escherichia coli* cells, followed by centrifugation to collect a target protein in the supernatant.

The sample solution was filtered using ULTRAFREE MC 0.45 μm Filter Unit (NIHON MILLIPORE K.K.), and the filtrate was applied to SP-5PW column (7.5×75 mm; TOSOH CORPORATION), followed by elution of a target protein using 50 mM MES buffer (pH 6.0) as a mobile phase at a flow rate of 1 mL/min under a linear concentration gradient of sodium chloride.

Figure 4:
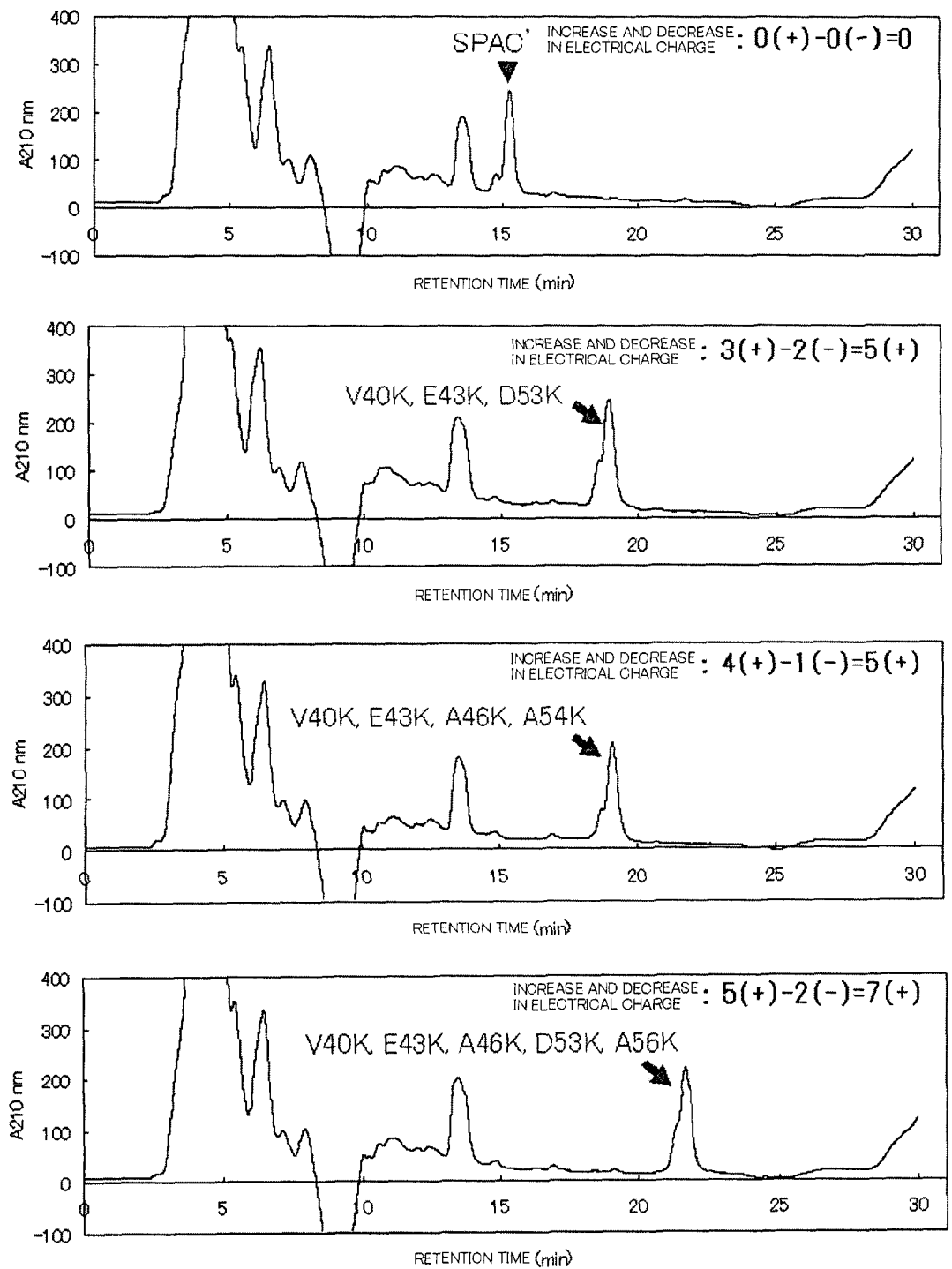
FIG. 4 A drawing showing behaviors of immunoglobulin-binding protein variants in cation exchange chromatography.

FIG. 4 shows behaviors of modified proteins obtained by adding three to five lysine to an immunoglobulin-binding protein in cation exchange chromatography. The results revealed that the increase in positive electric charge due to the increase in the number of lysine residues caused the increase in affinity of the immunoglobulin-binding proteins for the cation exchange column, resulting in elution of the proteins at higher concentrations of sodium chloride. As a result, it was found that a modified protein where lysine was introduced could be easily separated from contaminating proteins derived from *Escherichia coli*.

Note that the immunoglobulin-binding protein used in this study includes a His-tag on the C-terminal, and SPAC' with no His-tag has a pKa value lower by about 1 than that of a protein with a His-tag. Therefore, in the case where a modified protein with no His-tag used as an immunoglobulin affinity ligand is purified, the modification of the present invention is more effective on an increase in positive charge. That is, FIG. 4 shows that the immunoglobulin affinity ligands of the present invention enable dramatically simplified and low-cost production steps of the ligands as compared to a conventional ligand.

EXAMPLE 3

[Study on Stability of Modified Immunoglobulin-Binding Protein Where Aspartic Acid-Proline Sequence is Eliminated Under Acidic pH Conditions]

SPAC' purified in accordance with Example 2 and a modified immunoglobulin-binding protein with substitution of another amino acid for the aspartic acid at position 37 were incubated at a protein concentration of 0.5 mg/mL in water or 50% formic acid at 37° C. for 24 hours.

The resultant solutions were diluted 50-fold with 50% acetonitrile containing 0.1% trifluoroacetic acid, and 1 μL of the diluted solutions were spotted on an NP20 tip and analyzed using SELDI-TOF MS (Bio-Rad Laboratories, Inc.).

Figure 5:
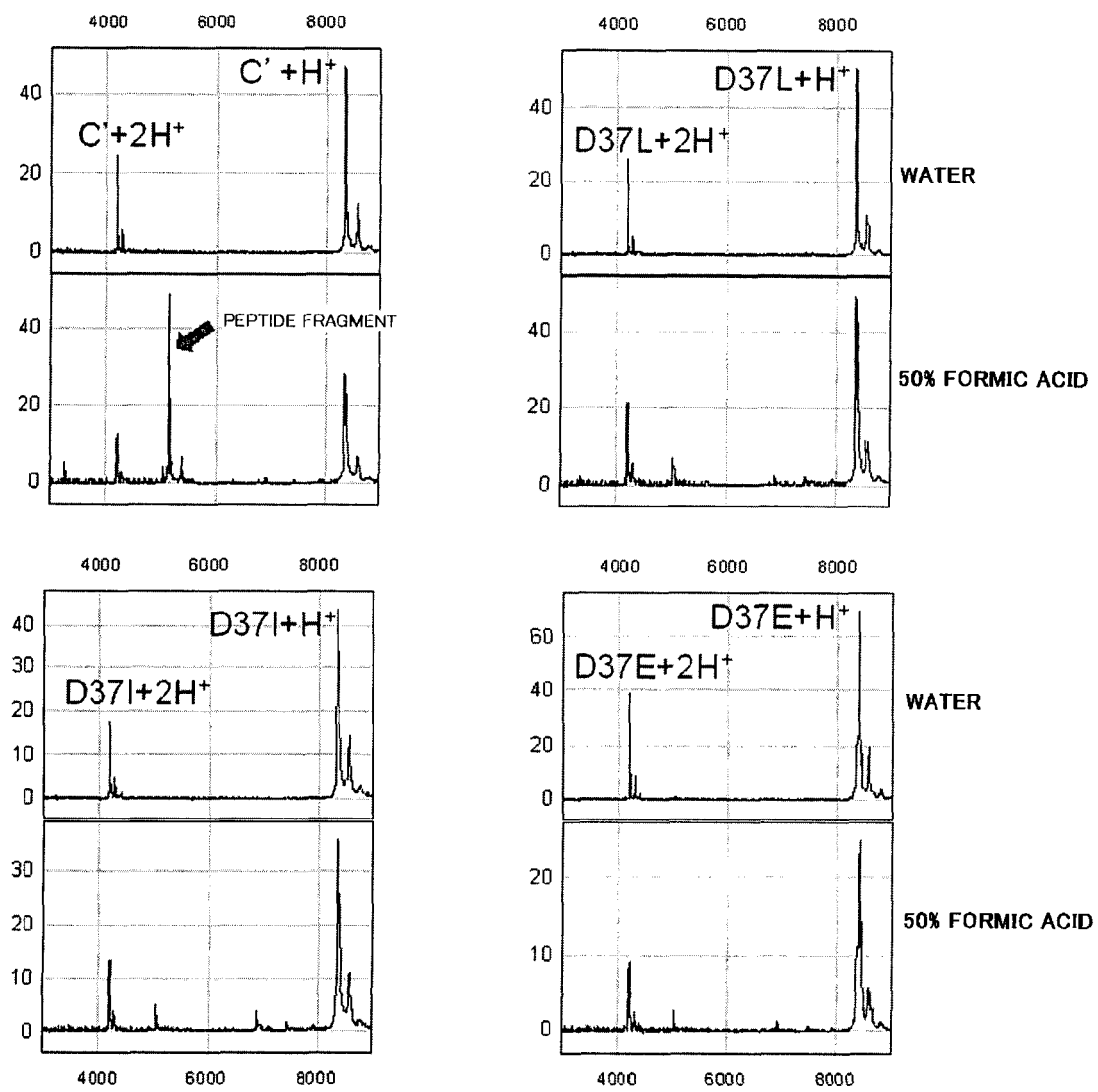
FIG. 5 A drawing showing comparison of cleavage properties of immunoglobulin-binding proteins treated under acidic pH conditions.

As shown in FIG. 5, in the case of the sample of SPAC' treated under acidic pH conditions, a peptide fragment obtained by cleavage between aspartic acid and proline at positions 37 and 38 was detected by mass spectrometry, while in the case of the sample of the modified protein obtained by treating the protein modified at position 37, no fragment was detected. That is, the results reveal that an unmodified immunoglobulin-binding protein is easily cleaved between aspartic acid and proline at positions 37 and 38 under acidic pH conditions, and the defect can be eliminated by amino acid substitution at position 37 of the present invention.

EXAMPLE 4

[Construction of Plasmid for Expressing Immunoglobulin-Binding Protein with no His-Tag]

PCR was performed using the plasmid for expressing a modified immunoglobulin-binding protein with a His-tag primarily prepared above as a template and using primers designed so as to have no sequence encoding a His-tag at the C-terminal site, to thereby obtain a target DNA fragment having no sequence encoding a His-tag.

The DNA fragment was cleaved with NdeI and BamHI and incorporated into a plasmid pET-9a to prepare a plasmid for expressing a modified immunoglobulin-binding protein with no His-tag.

Next, the overlap extension method (two-step PCR) was performed using a plasmid for expressing a modified protein having no sequence encoding a His-tag as a template and using the primers shown in Table 2 to introduce a mutation for causing amino acid substitution at positions 4, 7, and 35, followed by incorporation into the plasmid pET-9a in the same way as above, to thereby prepare a target expression plasmid. Then, PCR was performed using the resultant variant protein plasmid as a template and using primers for causing a mutation at another position, to thereby prepare a cDNA fragment of a variant protein including amino acid substitutions at a plurality of positions. In addition, the overlap extension method was performed using a combination of a cDNA fragment where mutation was introduced into a forward position of 35 and a cDNA fragment where mutation was introduced into a backward position of 35 to construct modified protein-expressing plasmids where amino acid on 2 to 10 sites were substituted.

The sequence numbers of the primers each represent the sequence numbers in Sequence Listing.

TABLE 2

| Variant protein | Sequence number of U-primer | Sequence number of R-primer |
|---|---|---|
| K4A | 22 | 23 |
| K7T | 24 | 25 |
| K7R | 26 | 27 |
| K35A | 28 | 29 |
| K35H | 30 | 31 |
| K35N | 32 | 33 |
| K35Q | 34 | 35 |
| K35R | 36 | 37 |
| K35Y | 38 | 39 |

EXAMPLE 5

[Expression and Purification of Immunoglobulin-Binding Protein with no His-Tag]

The nucleotide sequences of the constructed plasmids for expressing an immunoglobulin-binding protein with no His-tag were confirmed to be desired sequences, and BL21 (DE3) competent cells (Merck Ltd.) were transformed with the respective plasmids and cultured in the same way as in the case of expression of the immunoglobulin-binding protein with a His-tag, to thereby prepare Escherichia coli strains expressing target proteins.

The resultant Escherichia coli cells were suspended in 20 mM phosphate buffer (pH 6.0), and sonication was performed to break the Escherichia coli cells, followed by centrifugation to collect target proteins in the supernatant.

To the sample solutions were added 0.2 M acetic acid to adjust pH of the solutions to values lower by about 0.6 than the theoretical isoelectric point of the modified proteins, and the solutions were centrifuged again to collect target proteins in the supernatants. The solutions were filtered using ULTRAFREE MC 0.45 µm Filter Unit (NIHON MILLI-PORE K.K.), and the filtrates were applied to a column filled with TOYOPEARL gel SP-550C (5 mL; TOSOH CORPO-RATION), followed by elution and purification of target proteins using 50 mM sodium acetate buffer (pH 4.5) or 50 mM MES buffer (pH 6.0) as a mobile phase under a linear concentration gradient of sodium chloride.

The purity of the purified proteins was confirmed by sodium dodecyl sulfate-polyacrylamide gel electrophoresis, and the concentrations of the proteins were determined using BCA Protein Assay (Pierce Biotechnology Inc.).

As a result of the procedures, purified products each containing about 200 mg of a modified immunoglobulin-binding protein in 1 l of the culture medium were obtained.

EXAMPLE 6

[Immobilization of Modified Immunoglobulin-Binding Protein with No His-Tag on Chromatography Carrier]

A solution of a purified immunoglobulin affinity ligand of the present invention was subjected to gel filtration using Sephadex G-25 gel (GE Healthcare Bio-Sciences KK) to substitute a buffer for a ligand immobilization reaction (0.2 M sodium hydrogen carbonate buffer (pH 8.3) containing 0.5 M NaCl) for the buffer.

The ligand immobilization reaction was performed by: adding a ligand solution adjusted to a concentration of 2 mg/mL with respect to NHS-activated Sepharose 4-FF gel (GE Healthcare Bio-Sciences KK), which had been washed, in the same volume as the gel; and shaking the solution at 25° C. for 4 hours.

After the immobilization reaction, the supernatant of the reaction solution was collected and applied to TSK gel SuperSW column (4.6×300 mm; TOSOH CORPORATION), and the amount of unreacted ligands was measured by detecting unreacted ligand proteins at an absorbance of 280 nm by gel filtration chromatography using 50 mM phosphate buffer (pH 7.0) containing 0.5 M NaCl as a mobile phase, to thereby determine the amount of the ligand immobilized on the gel.

As a result, it was confirmed that all the immunoglobulin affinity ligands of the present invention were immobilized on the gel at 99% or more of the amounts of the ligands used in the immobilization reaction under the above-described conditions.

After the ligand immobilization reaction, the gel was shaken in a solution (pH 8.3) of 0.5 M ethanolamine containing 0.5 M NaCl at 25° C. for 1 hour to block unreacted NHS-activated groups, and washed with a 0.1 M sodium acetate solution (pH 4.0) containing 0.5 M NaCl and a 0.5 M ethanolamine solution (pH 8.3) containing 0.5 M NaCl alternately three times, and finally washed with phosphate buffered saline (hereinafter, referred to as PBS) three times, and the gel was used in measurement of the binding amount of the immunoglobulin.

EXAMPLE 7

[Measurement of Amount of Immunoglobulin-Binding to Affinity Gel Including Modified Immunoglobulin-Binding Protein as Ligand]

To a gel immobilized with a ligand was added an equal volume of a solution of 40 mg/mL human immunoglobulin (Sigma-Aldrich Corporation) in PBS, and the whole was shaken at 25° C. for 1 hour to adsorb the immunoglobulin on the gel. Thereafter, the gel was washed with PBS three times and shaken in 0.1 M glycine-HCl buffer (pH 2.8) at 25° C. for 10 minutes to elute the immunoglobulin from the gel.

A 1M Tris solution was added to the elute at a volume of 1/20 to neutralize the solution, and the absorbance at 280 nm was measured to determine the amount of the immunoglobulin adsorbed on the affinity gel based on the specific absorption coefficient of 13.8 (1 g-1 cm-1).

Figure 6:
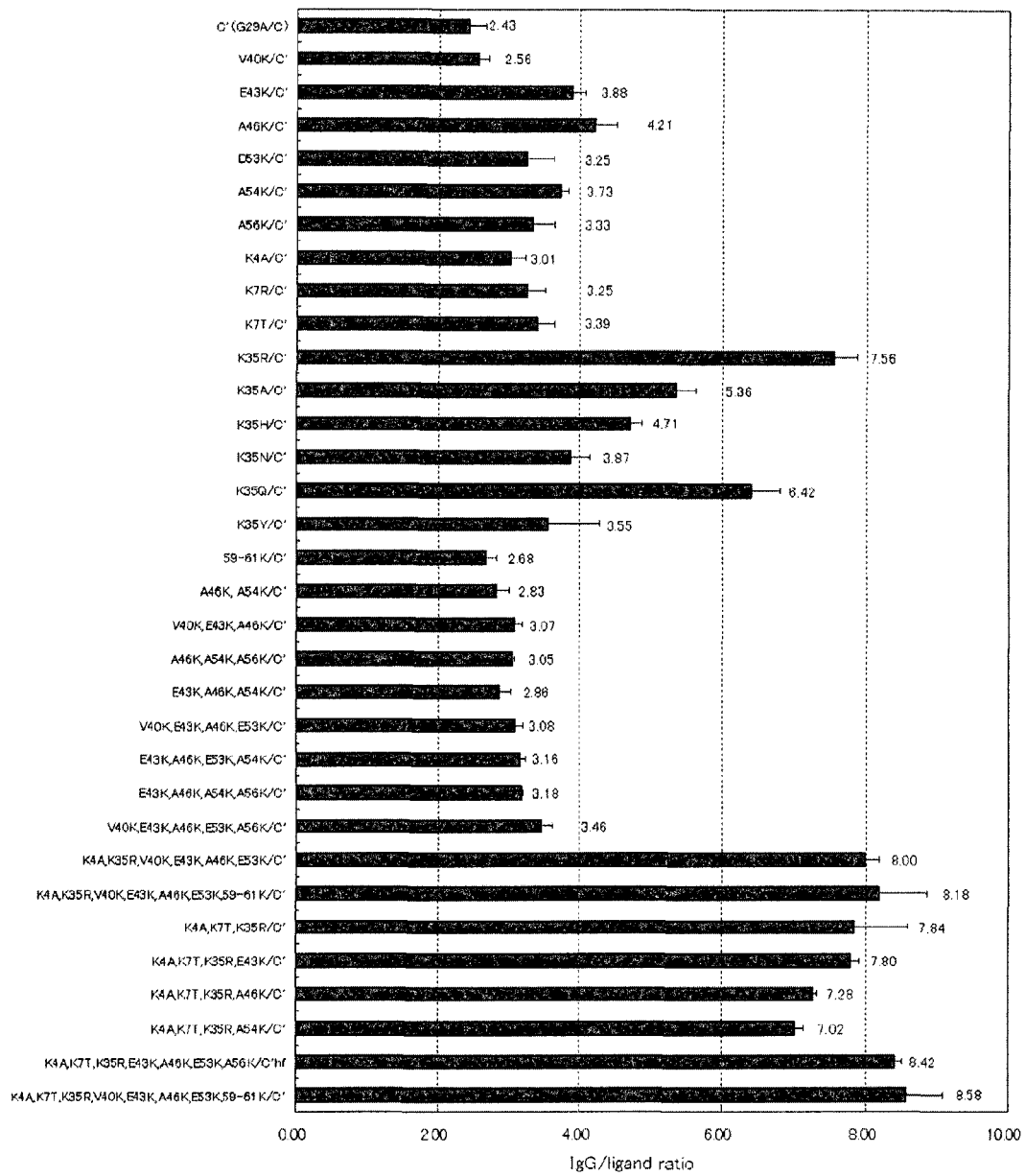
FIG. 6 A drawing showing comparison of IgG-binding abilities of immunoglobulin-binding proteins immobilized on chromatography carriers as affinity ligands.

FIG. 6 shows the results of evaluation of the immunoglobulin-binding activities of the immunoglobulin-binding proteins of the present invention, used as affinity ligands, which were determined based on values obtained by dividing the amounts (mg) of the immunoglobulins adsorbed on 1 ml of the gel by the amounts (mg) of the immobilized ligands (IgG/ligand ratio).

The best embodiment of the present invention for the immunoglobulin-binding activity at present is a modified protein that has been subjected to modification for substitution of amino acid other than a lysine for the lysines at positions 4, 7, and 35 in an immunoglobulin-binding domain of *Staphylococcus* protein A and substitution of lysine for 3 to 5 of the amino acids at positions 40, 43, 46, 53, and 56 on the protein surface of helix 3 and a modified protein with modification for addition of 3 lysines to the C-terminal in addition to the above modification, and the affinity gels containing such modified proteins as affinity ligands were found to have activities to bind to immunoglobulins, which are higher up to 3.5 times as compared to a gel containing an unmodified SPAC' domain.

Among amino acid sequence modifications included in the present invention, the modification for substitution of an amino acid other than a lysine for the lysine at position 35 is very effective for increasing the amount of an immunoglobulin adsorbed on a gel immobilized with a resultant protein as an affinity ligand. In particular, substitution of an arginine or glutamine was found to be the most effective. The results reveal that immobilization of an immunoglobulin-binding domain of protein A at position about 35 causes a significant decrease in the activity of the molecule to bind to an immunoglobulin. Note that an immunoglobulin-binding protein that is another protein derived from *Staphylococcus* and is different from protein A (described in Patent Document 1) includes a region having about 45% homology in the amino acid sequence with an immunoglobulin-binding domain of protein A, and arginine is present on the position corresponding to position 35 in the sequence. However, at positions 1 to 38, which are estimated to be an immunoglobulin-binding region in the above-described similar domain, lysine are present at three positions completely different from the immunoglobulin-binding domain of protein A, in particular, at position 32, and moreover, the number of lysine present at positions 39 onwards is smaller than that in an immunoglobulin-binding domain of protein A, and the ratio of the number of lysine at positions 39 onwards to the number of lysine at positions 1 to 38 is lower than that in the immunoglobulin-binding domain of protein A. Therefore, it is easily estimated that good orientation is very difficult to maintain in immobilization on a carrier via a lysine residue. That is, it is obvious that the modified protein of the present invention has structural and functional properties that are very useful as an affinity ligand for an immunoglobulin as compared to the protein described in Patent Document 1.

EXAMPLE 8

[Study on Stability of Affinity Gel Containing Modified Immunoglobulin-Binding Protein as Ligand Under Alkaline pH Conditions]

An affinity gel containing a modified immunoglobulin-binding protein as a ligand was incubated in a 0.1 N NaOH solution at 25° C. at a certain period of time and washed with PBS three times, and the binding amount of the immunoglobulin was measured in accordance with the method described in Example 7.

Figure 7:
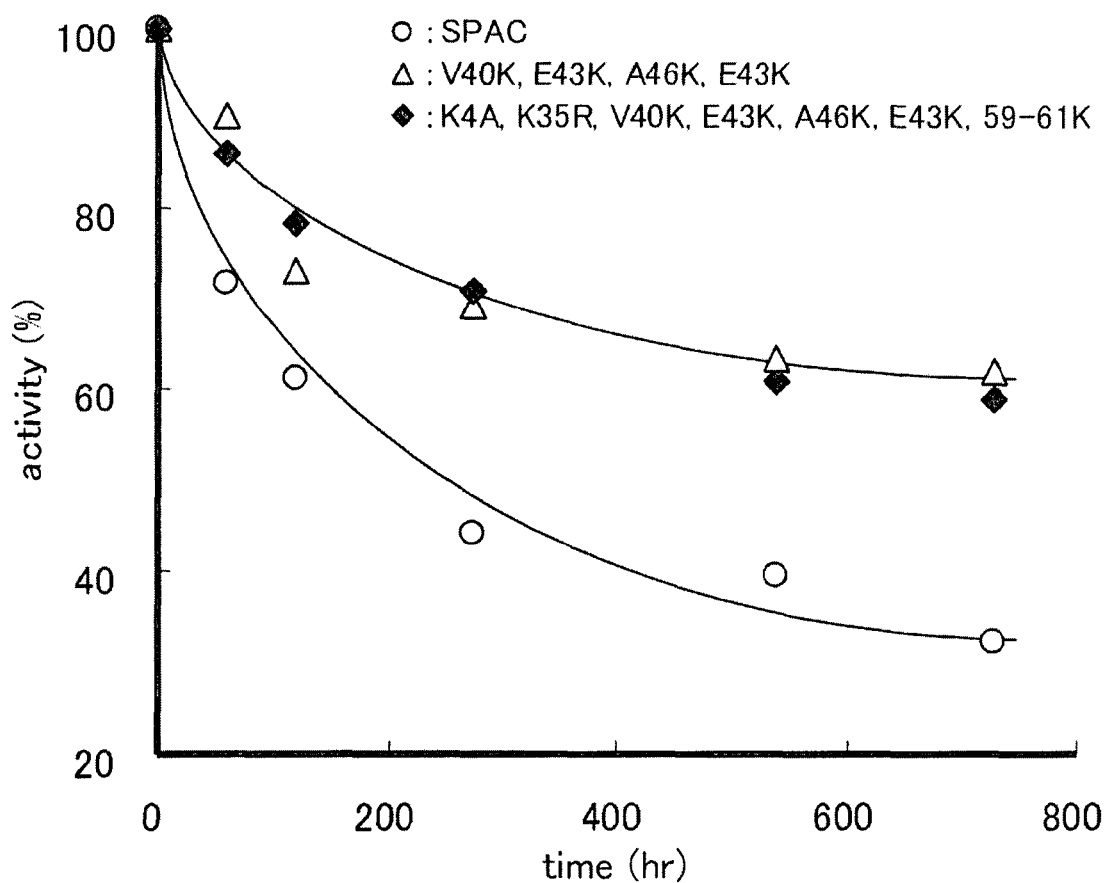
FIG. 7 A drawing showing comparison of remaining activities of affinity gels including immunoglobulin-binding proteins as ligands when the gels are treated under alkaline pH conditions.

The gel was treated under alkaline pH conditions, and the binding amounts of the immunoglobulin were measured at the respective treatment time periods, and the residual ratios calculated based on the binding amount of the immunoglobulin before the treatment under alkaline pH conditions as 100% are shown in FIG. 7.

The results show that the immunoglobulin affinity ligands of the present invention, which were obtained by modifying an immunoglobulin-binding domain of *Staphylococcus* protein A so that lysine residues on the protein surface of helix 3 are increased, are stable against the treatment under alkaline pH conditions as compared to an unmodified ligand when the ligands are immobilized on the affinity gel.

INDUSTRIAL APPLICABILITY

An affinity chromatography carrier containing an immunoglobulin-binding protein of the present invention is inexpensive, has high immunoglobulin-binding capability, and a little leakage of a ligand protein. That is, the present invention is useful for construction of a production process for an inexpensive and high-quality immunoglobulin, an antibody-immobilized tip or microplate to be used in diagnosis, a safe hemopurification system for removing an immunoglobulin, and the like.

The invention claimed is:

1. An immunoglobulin-binding protein, comprising:
a variant of the amino acid sequence of SEQ ID NO: 1 representing a modified C-domain of *Staphylococcus* protein A or a variant of the amino acid sequence of SEQ ID NO: 2 representing a Z-domain, said variant being identical to said SEQ ID NO: 1 or said SEQ ID NO:2 except
(a) the lysine residue of position 35 of SEQ ID NO: 1 or SEQ ID NO: 2 is substituted with an arginine residue; or
(b) the lysine residues of positions 4, 7, and 35 of SEQ ID NO: 1 or SEQ ID NO: 2 are substituted with amino acids other than a lysine residue; or
(c) one or more of amino acid residues of positions 40, 43, 46, 53, 54, and 56 of SEQ ID NO: 1 or SEQ ID NO: 2 are substituted with lysine residues, in addition to said modification (b);
(d) in addition to the changes set forth as (a)-(c) above, the immunoglobulin-binding protein optionally comprises a substitution of the aspartic acid residue at position 37 of SEQ ID NO:1 or SEQ ID NO:2 with an amino acid residue other than aspartic acid;
wherein said immunoglobulin-binding protein has an improved orientation for maintaining affinity for an immunoglobulin in immobilization of the protein on an insoluble carrier via amino groups of the protein as compared to a molecule which does not have said modifications (a)-(d).

2. The immunoglobulin-binding protein according to claim 1, wherein the protein comprises the modification (b), and wherein the lysine residues of the positions 4, 7, and 35 are substituted with an alanine, glutamine, asparagine, valine, serine, threonine, histidine, tyrosine, or arginine residue.

3. The immunoglobulin-binding protein according to claim 1, wherein in addition to the modifications according to claim 1, the aspartic acid residue of the position of 37 of SEQ ID NO: 1 or SEQ ID NO: 2 is substituted with an amino acid residue other than an aspartic acid residue.

4. The immunoglobulin-binding protein according to claim 3, wherein the aspartic acid residue of the position of 37 is substituted with an alanine, glutamic acid, serine, threonine, leucine, or isoleucine residue.

5. The immunoglobulin-binding protein according to claim 1, comprising the amino acid sequence specified by SEQ ID NO: 3.

6. A multimer, comprising:
2 to 5 of tandemly linked immunoglobulin-binding proteins which comprise the immunoglobulin-binding protein according to claim 1.

7. A nucleic acid, comprising a nucleic acid which encodes the immunoglobulin-binding protein according to claim 1, or the multimer comprising the immunoglobulin-binding protein according to claim 6.

8. A gene expression system, comprising the nucleic acid according to claim 7.

9. An affinity chromatography carrier, comprising, as an affinity ligand, the immunoglobulin-binding protein according to claim 1 or the multimer comprising the immunoglobulin-binding protein according to claim 6.

10. An affinity column, comprising the affinity chromatography according to claim 6.

11. An affinity separation method for IgG, IgA, and/or IgM, the method comprising:
   immobilizing the immunoglobulin-binding protein according to claim 1 on a carrier,
   filling an affinity column with the carrier having the immunoglobulin-binding protein, and
   separating IgG, IgA, and/or IgM from a sample by allowing the sample to pass through the affinity column, while allowing IgG, IgA, and/or IgM in the sample to bind to the immunoglobulin-binding protein.

12. A protein chip, comprising the immunoglobulin-binding protein according to claim 1 or the multimer according to claim 6.

* * * * *